(12) United States Patent
Jordan et al.

(10) Patent No.: US 11,118,208 B2
(45) Date of Patent: Sep. 14, 2021

(54) METHODS FOR MODULATING PROTEIN GALACTOSYLATION PROFILES OF RECOMBINANT PROTEINS USING PERACETYL GALACTOSE

(71) Applicant: ARES TRADING S.A., Aubonne (CH)

(72) Inventors: Martin Jordan, Ecublens (CH); Gabrielle Leclercq, Lausanne (CH); Jonathan Souquet, Blonay (CH); Herve Broly, Chatel-St-Denis (CH); David Bruhlmann, Lausanne (CH)

(73) Assignee: ARES TRADING S.A., Aubonne (CH)

( * ) Notice: Subject to any disclaimer, the term of this patent is extended or adjusted under 35 U.S.C. 154(b) by 85 days.

(21) Appl. No.: 16/300,066

(22) PCT Filed: May 10, 2017

(86) PCT No.: PCT/EP2017/061181
§ 371 (c)(1),
(2) Date: Nov. 9, 2018

(87) PCT Pub. No.: WO2017/194605
PCT Pub. Date: Nov. 16, 2017

(65) Prior Publication Data
US 2019/0153497 A1   May 23, 2019

(30) Foreign Application Priority Data

May 10, 2016 (EP) .................................. 16169062

(51) Int. Cl.
| | |
|---|---|
| *C12P 21/00* | (2006.01) |
| *C12P 21/08* | (2006.01) |
| *C12N 5/00* | (2006.01) |
| *C07K 16/00* | (2006.01) |
| *A61K 39/395* | (2006.01) |
| *C12N 5/071* | (2010.01) |
| *A61K 38/00* | (2006.01) |

(52) U.S. Cl.
CPC .......... *C12P 21/005* (2013.01); *A61K 39/395* (2013.01); *C07K 16/00* (2013.01); *C12N 5/0682* (2013.01); *A61K 38/00* (2013.01); *C07K 2317/14* (2013.01); *C07K 2317/41* (2013.01); *C12N 2500/34* (2013.01); *C12N 2510/02* (2013.01)

(58) Field of Classification Search
CPC .... C07K 16/00; C07K 2317/41; C07H 13/04; C12N 2500/34; C12N 2510/02; C12N 5/0682; A61K 39/395; C12P 21/005
USPC ........................................ 435/69.6, 404, 405
See application file for complete search history.

(56) References Cited

U.S. PATENT DOCUMENTS

2013/0129784 A1   5/2013  Senter et al.

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Hodoniczky, J. et al. "Control of Recombinant Monoclonal Antibody Effector Functions by Fc N-Glycan Remodeling in Vitro" *Biotechnology Progress*, Oct. 7, 2005, pp. 1644-1652, vol. 21, No. 6.
Written Opinion in International Application No. PCT/EP2017/061181, dated Jul. 28, 2017, pp. 1-5.

* cited by examiner

*Primary Examiner* — Robert B Mondesi
*Assistant Examiner* — Mohammad Y Meah
(74) *Attorney, Agent, or Firm* — Saliwanchik, Lloyd & Eisenschenk

(57) ABSTRACT

The present invention relates to methods and compositions for modulating glycosylation profile, such as the galactosylation profile, of recombinant proteins expressed by mammalian host cells during the cell culture process by supplementing cell culture media with a peracetyl galactose.

6 Claims, 12 Drawing Sheets

METHODS FOR MODULATING PROTEIN GALACTOSYLATION PROFILES OF RECOMBINANT PROTEINS USING PERACETYL GALACTOSE

CROSS-REFERENCE TO RELATED APPLICATION

This application is the U.S. national stage application of International Patent Application No. PCT/EP2017/061181, filed May 10, 2017.

FIELD OF THE INVENTION

The present invention relates to methods and compositions for modulating galactosylation profile of recombinant proteins expressed by mammalian host cells during the cell culture process, using peracetyl galactose.

BACKGROUND OF THE INVENTION

The glycosylation profile of a protein, such as a therapeutic protein or an antibody, is an important characteristic that influences biological activity of the protein through changes in half-life and affinity due to effects for instance on folding, stability and antibody-dependent cellular cytotoxicity (ADCC, one of the mechanism responsible for the therapeutic effect of antibodies)(Eon-Duval et al., 2012). Glycosylation is highly dependent on the cell line that is used for the production of the protein of interest, as well as on the cell culture processes (pH, temperature, cell culture media composition, raw material lot-to-lot variation, medium filtration material, air, etc.).

ADCC activity is influenced by the amount of fucose and/or mannose linked to the oligosaccharides of the Fc region, with enhanced activity seen with a reduction in fucose and/or an increase in mannose. Indeed, for instance, compared to fucosylated IgGs, non-fucosylated forms exhibit dramatically enhanced ADCC due to the enhancement of FcγRIIIa binding capacity without any detectable change in complement-dependent cytotoxicity (CDC) or antigen binding capability (Yamane-Ohnuki and Satoh, 2009). Similarly, antibodies exhibiting high level of mannose-5 glycans also presented higher ADCC (Yu et al., 2012). Thus, where the ADCC response is the principle therapeutic mechanism of antibody activity, the provision of methods for the preparation of recombinant therapeutic protein with a glycosylation profile characterized by decreased fucosylation and/or increased mannosylation, are beneficial. The advantages of non-fucosylated and/or highly mannosylated antibodies also include achieving therapeutic efficacy at low doses. However, many therapeutic antibodies that are currently on the market are heavily fucosylated because they are produced by mammalian cell lines with intrinsic enzyme activity responsible for the core-fucosylation of the Fc N-glycans of the products.

Galactosylation: has also an impact on the activity of the antibodies. Although it does not appear to affect the antibody binding to antigen, it has been reported that changes in galactosylation may result in noticeable changes in CDC activity of some recombinant IgGs (Hodoniczky et al., 2005). Indeed, it was demonstrated that degalactosylation of Rituxan reduced CDC by approximately half, relative to unmodified (variably galactosylated) control Mab.

Modulation of protein glycosylation is of particular relevance for marketed therapeutic proteins or antibodies as glycosylation (such as galactosylation) can impact therapeutic utility and safety. Further, in the frame of biosimilar compounds, control of the glycosylation profile of a recombinant protein is crucial, as the glycosylation profile of said recombinant protein has to be comparable to the glycosylation profile of the reference product.

Therefore, there remains a need for culture conditions and production methods that allow controlling the glycosylation profile, such as galactosylation profiles, of a recombinant protein. The present invention addresses this need by providing methods and compositions for modulating recombinant protein glycosylation, such as recombinant protein galactosylation.

SUMMARY OF THE INVENTION

In one aspect the invention provides a method of producing a recombinant protein with a modulated galactosylation profile, said method comprising culturing a host cell expressing said protein in cell culture medium supplemented with a peracetyl galactose.

Alternatively, here is disclosed a method of producing a recombinant protein with a modulated galactosylation profile, said method comprising culturing a host cell expressing said protein in cell culture medium complemented with at least one feed comprising a peracetyl galactose.

In a further aspect, the invention provides a composition comprising a cell culture medium comprising a peracetyl galactose.

In another aspect, the invention provides a pharmaceutical composition comprising the recombinant protein with a modulated galactosylation profile produced by the methods of the invention and a pharmaceutically acceptable carrier.

In another aspect, the invention provides a composition comprising a recombinant protein with a modulated galactosylation profile produced by the methods of the invention.

In a further aspect, the invention provides use of a peracetyl galactose for modulating the galactosylation profile of recombinant proteins.

The peracetyl galactose is for instance α-2-F peracetyl galactose or β-2-F peracetyl galactose.

for mAb1 cells cultured at different α-2F-pGal concentrations in TubeSpin®. Results are presented as mean±standard deviation. The legend for FIG. 4A also applies to FIG. 4B. The concentrations which are mentioned refer to the concentrations at day 0, just after the inoculation.

Figure 5:
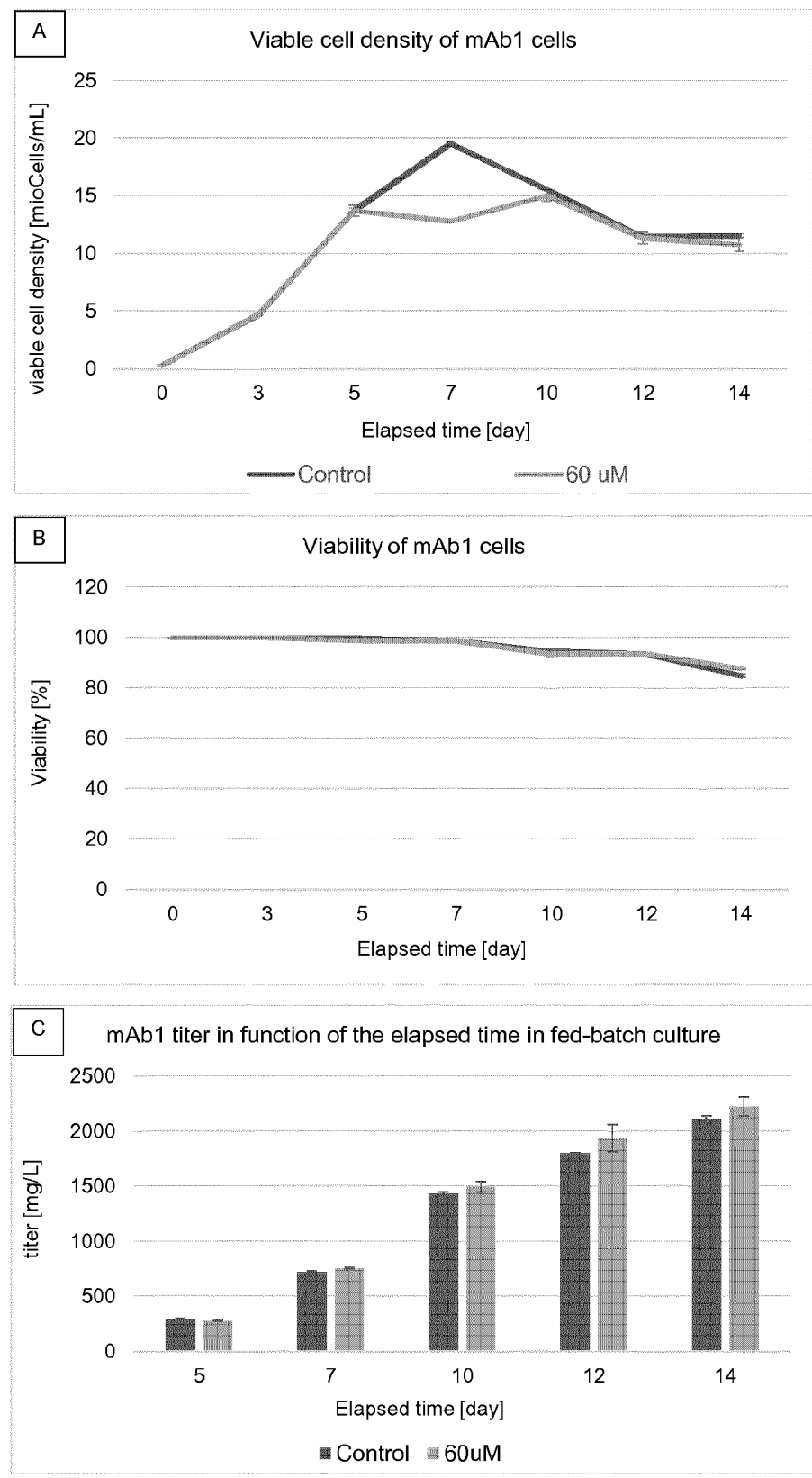

FIG. 5 shows density of viable cells (FIG. 5A; ViCell®) and viability (FIG. 5B; ViCell®) in relation to time as well as titer in relation to the elapsed time (FIG. 5C; Biacore®) for mAb1 cells cultured at different β-2F-pGal concentrations in TubeSpin®. Results are presented as mean±standard deviation. The concentrations which are mentioned refer to the concentrations at day 0, just after the inoculation.

Figure 6:
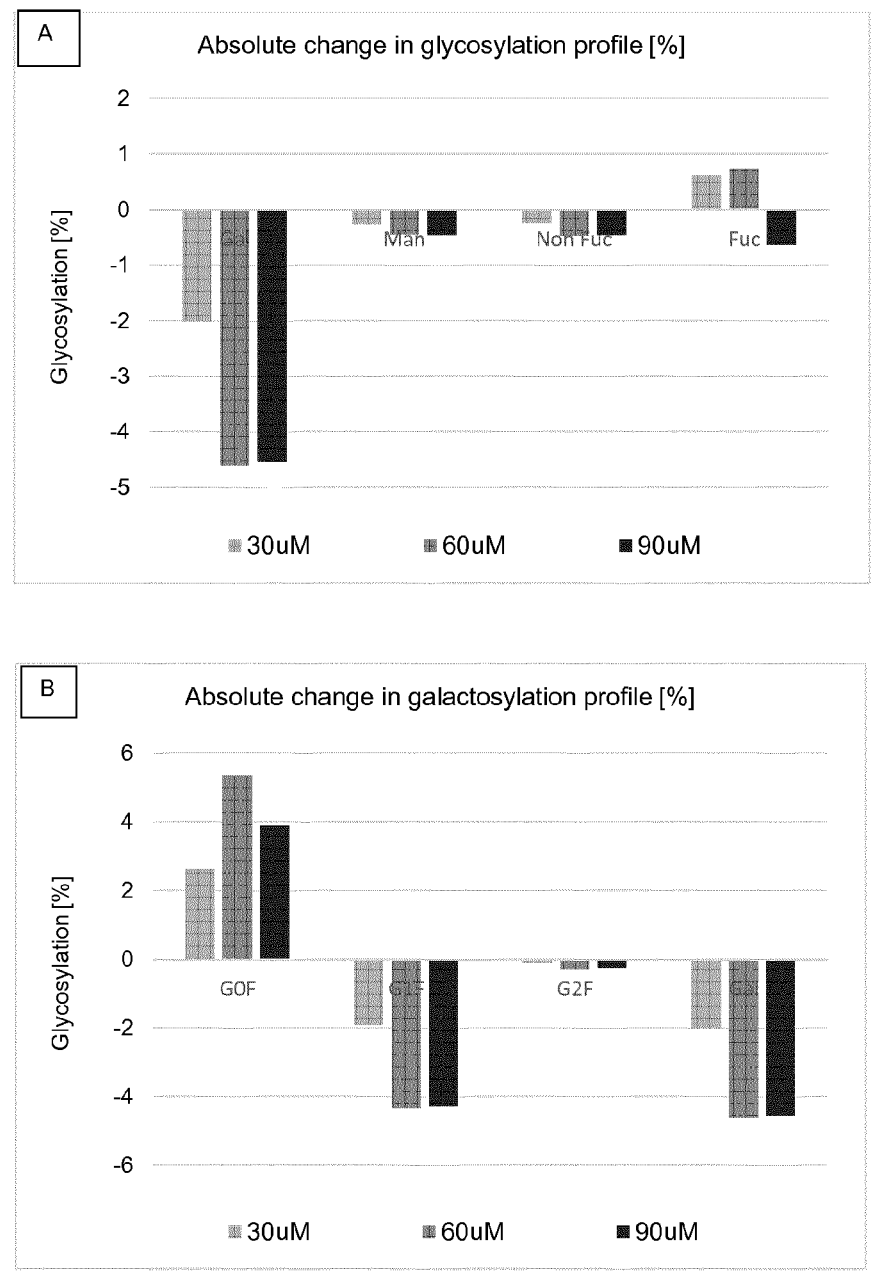

FIG. 6 shows the absolute change in glycosylation profile compared to control according to α-2F-pGal media concentration (FIG. 6A); as well as the absolute change in galactosylation profile compared to control according to α-2F-pGal media concentration (FIG. 6B).

Figure 7:
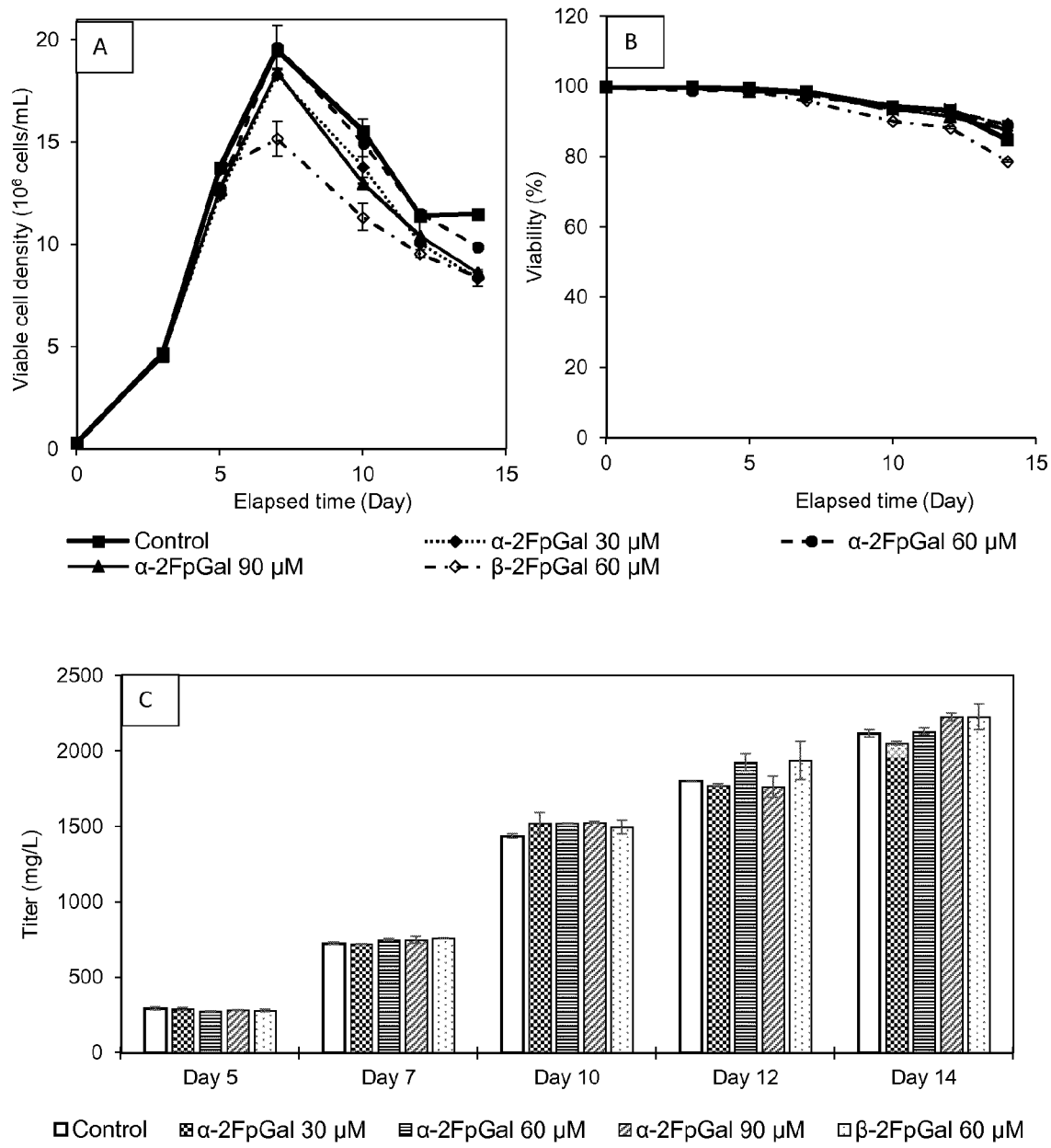

FIG. 7 shows (A) Viable cell densities of cell line A cultures supplemented with 0-90 µM α-2F-peracetyl-galactose or 60 µM β-2F-peracetyl-galactose in Shake Tubes. (B) Viabilities. (C) Protein titer for each concentration on culture days 5, 7, 10, 12 and 14. Each condition was conducted in duplicates. All points are mean values of the corresponding conditions and the error bars report the maximum and minimum values.

Figure 8:
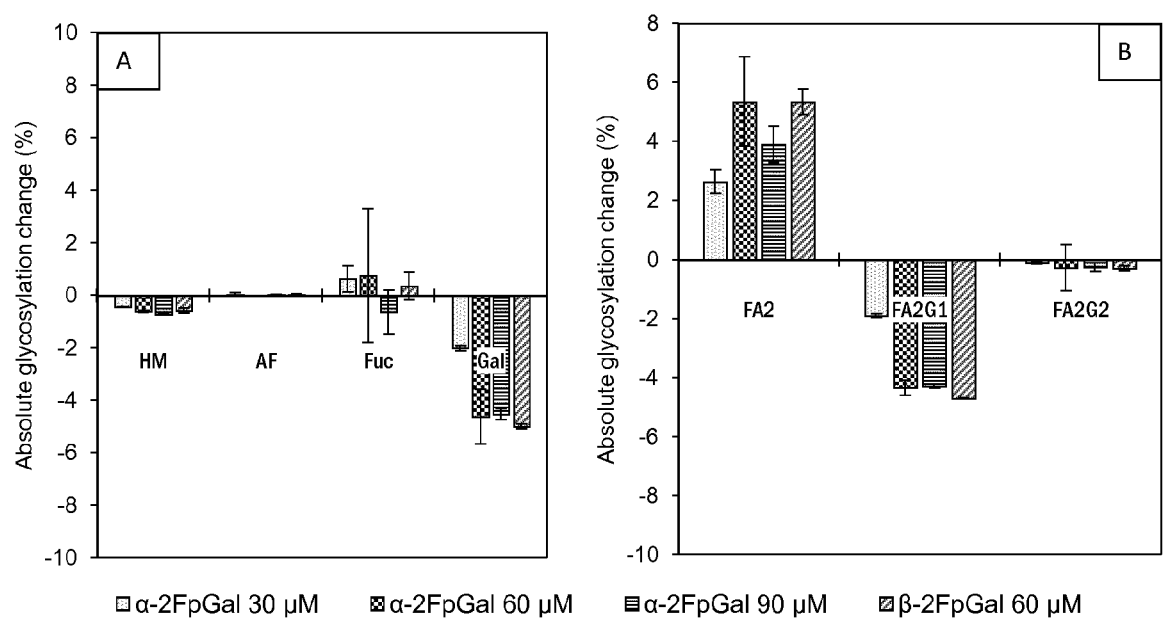

FIG. 8 shows (A) Absolute change of the overall glycosylation pattern compared to the control in function of the α- and β-2F-p-galactose concentration in medium in cell line A cultures. (B) Absolute change of galactosylation compared to the control in function of the α- and β-2F-p-galactose concentration in medium. Each condition was conducted in duplicates. All bars represent mean values of the corresponding conditions analyzed by CGE-LIF and the error bars report the maximum and minimum values.

Figure 9:
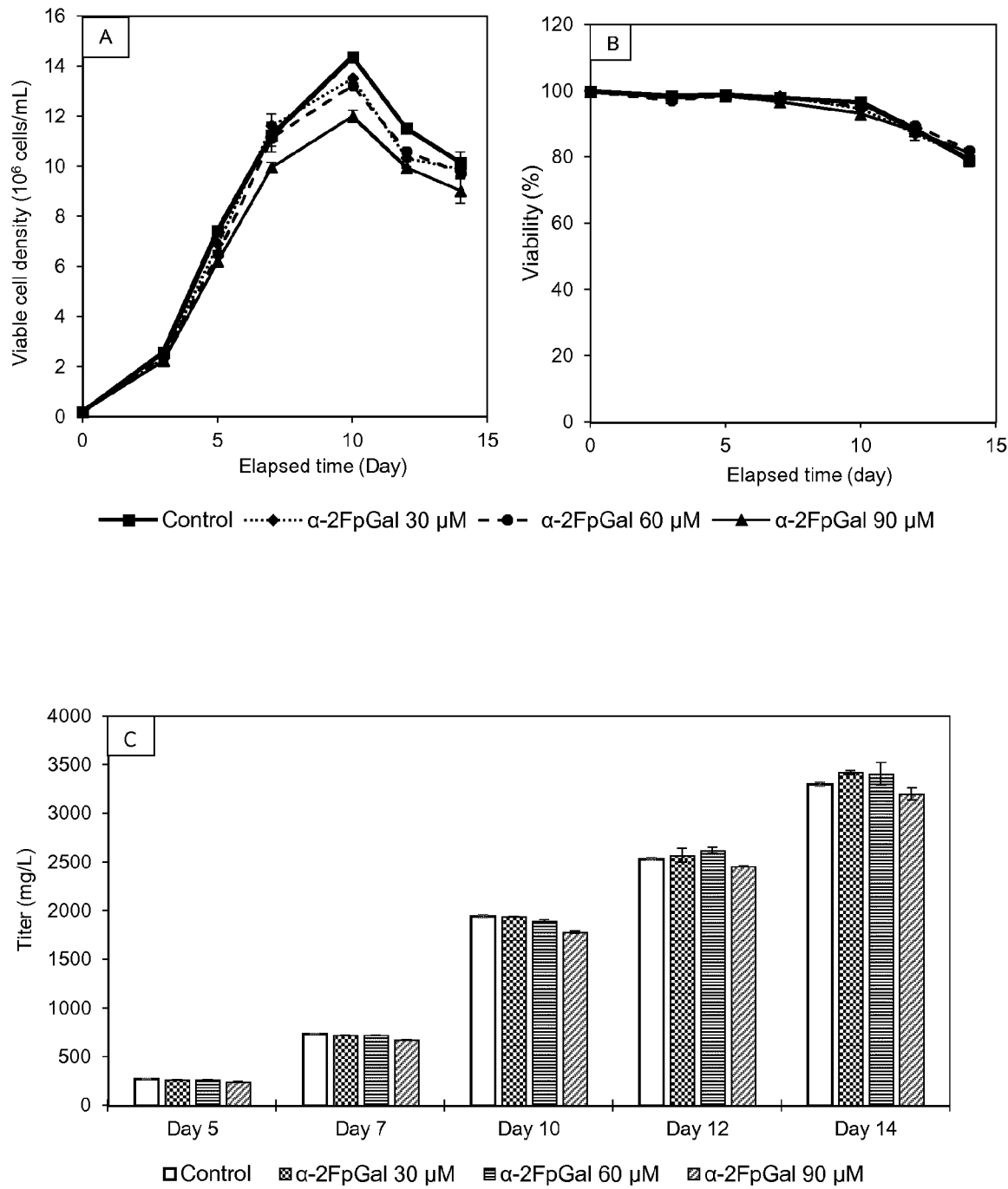

FIG. 9 shows (A) Viable cell densities of cell line B cultures supplemented with 0-90 µM α-2Fperacetyl-galactose in shake tubes. (B) Viabilities. (C) Protein titer for each concentration on culture days 5, 7, 10, 12 and 14. Each condition was conducted in duplicates. All points are mean values of the corresponding conditions and the error bars report the maximum and minimum values.

Figure 10:
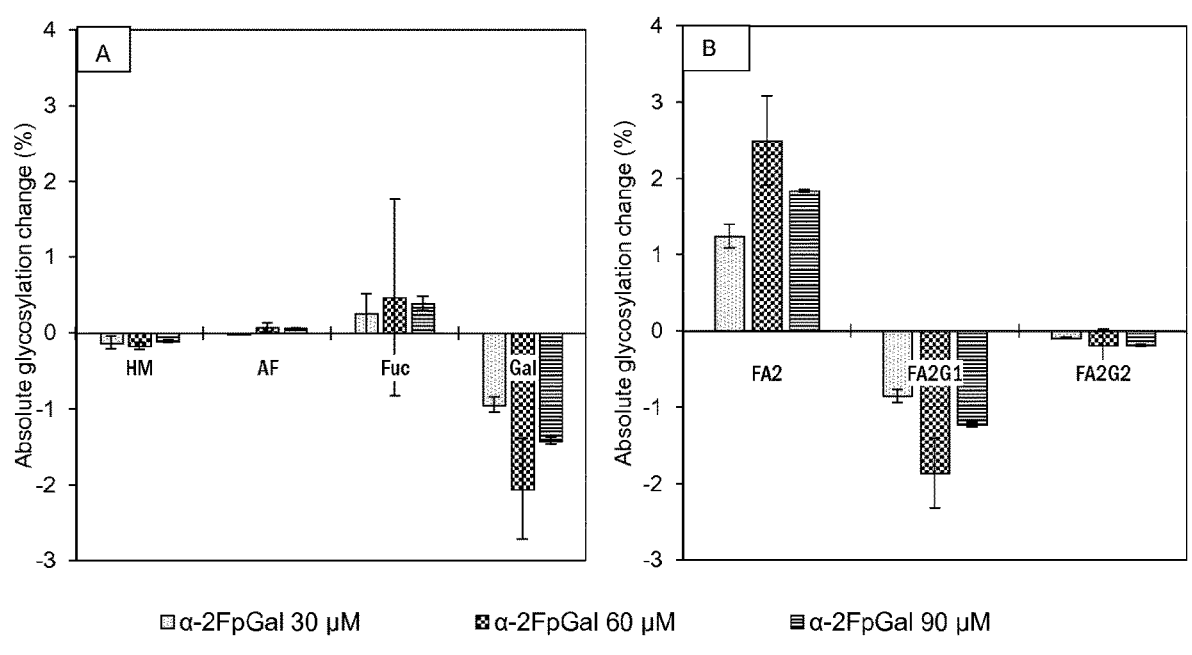

FIG. 10 shows (A) Absolute change of the overall glycosylation pattern compared to the control in function of the α-2F-p-galactose concentration in medium of cell line B cultures. (B) Absolute change of galactosylation compared to the control in function of the α-2F-p-galactose concentration in medium of cell line B cultures. Each condition was conducted in duplicates and analyzed by 2AB-UPLC. All bars represent mean values of the corresponding conditions and the error bars report the maximum and minimum values.

Figure 11:
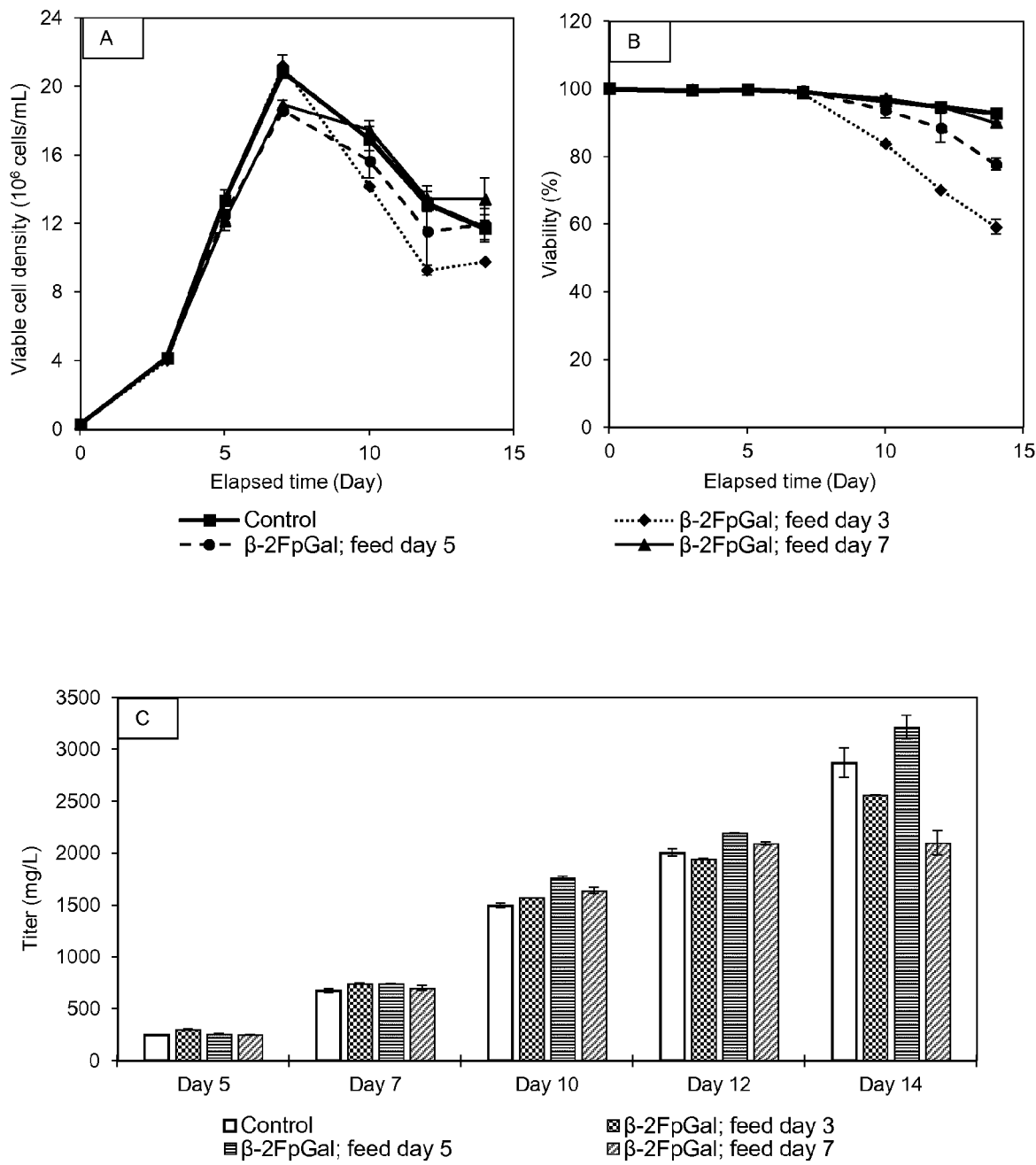

FIG. 11 shows (A) Viable cell densities of cell line A cultures in function of the feed timing of β-2F-p-galactose in shake tubes. (B) Viabilities. (C) Protein titer for each condition on culture days 5, 7, 10, 12 and 14. Experiments were conducted in duplicates. All points are mean values of the corresponding conditions and the error bars report the maximum and minimum values.

Figure 12:
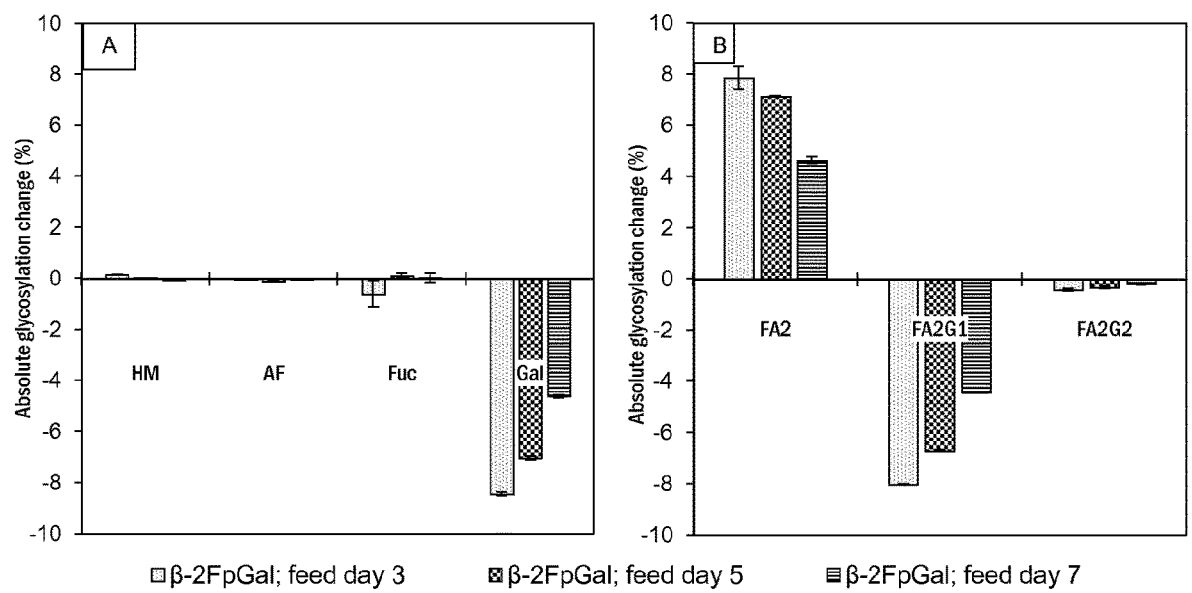

FIG. 12 shows (A) Absolute change of the overall glycosylation pattern compared to the control in function of the feed timing of β-2F-p-galactose in cell line A cultures. (B) Absolute change of galactosylation compared to the control in function of the feed timing of β-2F-p-galactose in cell line A cultures. Experiments were conducted in duplicates and supernatant analyzed by CGE-LIF. All bars represent mean values of the corresponding conditions and the error bars report the maximum and minimum values.

DETAILED DESCRIPTION OF THE INVENTION

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "and/or" used in a phrase such as "A and/or B" herein is intended to include "A and B", "A or B", "A", and "B".

The term "cell culture" or "culture" is meant the growth and propagation of cells in vitro, i.e. outside of an organism or tissue. Suitable culture conditions for mammalian cells are known in the art, such as taught in Cell Culture Technology for Pharmaceutical and Cell-Based Therapies (2005). Mammalian cells may be cultured in suspension or while attached to a solid substrate.

The terms "cell culture medium," "culture medium", "medium," and any plural thereof, refer to any medium in which cells of any type can be cultured. A "basal medium" refers to a cell culture medium that contains all of the essential ingredients useful for cell metabolism. This includes for instance amino acids, lipids, carbon source, vitamins and mineral salts. DMEM (Dulbeccos' Modified Eagles Medium), RPMI (Roswell Park Memorial Institute Medium) or medium F12 (Ham's F12 medium) are examples of commercially available basal media. Alternatively, said basal medium can be a proprietary medium fully developed in-house, also herein called "chemically defined medium" or "chemically defined culture medium", in which all of the components can be described in terms of the chemical formulas and are present in known concentrations. The culture medium can be free of proteins and/or free of serum, and can be supplemented by any additional compound(s) such as amino acids, salts, sugars, vitamins, hormones, growth factors, depending on the needs of the cells in culture.

The term "feed medium" or "feed" (and plural thereof) refers to a medium used as a supplementation during culture to replenish the nutrients which are consumed. The feed medium can be a commercially available feed medium or a proprietary feed medium (herein alternatively chemically defined feed medium).

The term "bioreactor" or "culture system" refers to any system in which cells can be cultured, preferably in batch or fed-batch mode. This term includes but is not limited to flasks, static flasks, spinner flasks, tubes, shake tubes, shake bottles, wave bags, bioreactors, fiber bioreactors, fluidized bed bioreactors, and stirred-tank bioreactors with or without microcarriers. Alternatively, the term "culture system" also includes microtiter plates, capillaries or multi-well plates. Any size of bioreactor can be used, for instance from 0.1 milliliter (0.1 mL, very small scale) to 20000 liters (20000

L or 20 KL, large scale), such as 0.1 mL, 0.5 mL 1 mL, 5 mL, 0.01 L, 0.1 L, 1 L, 2 L, 5 L, 10 L, 50 L, 100 L, 500 L, 1000 L (or 1 KL), 2000 L (or 2 K), 5000 L (or 5 KL), 10000 L (or 10 KL), 15000 L (or 15 KL) or 20000 L (20 KL).

The term "fed-batch culture" refers to a method of growing cells, where there is a bolus or continuous feed media supplementation to replenish the nutrients which are consumed. This cell culture technique has the potential to obtain high cell densities in the order of greater than $10 \times 10^6$ to $30 \times 10^6$ cells/ml, depending on the media formulation, cell line, and other cell growth conditions. A biphasic culture condition can be created and sustained by a variety of feed strategies and media formulations.

Alternatively a perfusion culture can be used. Perfusion culture is one in which the cell culture receives fresh perfusion feed medium while simultaneously removing spent medium. Perfusion can be continuous, step-wise, intermittent, or a combination of any or all of any of these. Perfusion rates can be less than a working volume to many working volumes per day. Preferably the cells are retained in the culture and the spent medium that is removed is substantially free of cells or has significantly fewer cells than the culture. Perfusion can be accomplished by a number of cell retention techniques including centrifugation, sedimentation, or filtration (see for example Voisard et al., 2003).

When using the methods and/or cell culture techniques of the instant invention, the protein with a modulated galactosylation profile are generally directly secreted into the culture medium. Once said protein is secreted into the medium, supernatants from such expression systems can be first concentrated using a commercially available protein concentration filter.

As used herein, "cell density" refers to the number of cells in a given volume of culture medium. "Viable cell density" refers to the number of live cells in a given volume of culture medium, as determined by standard viability assays. The cell density will be considered as maintained if it is in the range of about −10% to +10% compared to the control culture condition.

The term "viability", or "cell viability" refers to the ratio between the total number of viable cells and the total number of cells in culture. Viability is usually acceptable as long as it is at not less than 60% compared to the start of the culture (however, the acceptable threshold can be determined case by case). Viability is often used to determine time for harvest. For instance, in fed-batch culture, harvest can be performed once viability reaches at 60% or after 14 days in culture.

The wording "titre" refers to the amount or concentration of a substance, here the protein of interest, in solution. It is an indication of the number of times the solution can be diluted and still contain detectable amounts of the molecule of interest. It is calculated routinely for instance by diluting serially (1:2, 1:4, 1:8, 1:16, etc.) the sample containing the protein of interest and then using appropriate detection method (colorimetric, chromatographic etc.), each dilution is assayed for the presence of detectable levels of the protein of interest. Titre can also be measured by means such as by forteBIO Octet® or with Biacore C®, as used in the example section. The term "specific productivity" refers to the amount of a substance, here the protein of interest, produced per cell per day. The titre or specific productivity will be considered as maintained if it is in the range of about −10% to +10% compared to the control culture condition.

The term "modulated glycosylation profile" or "modulated glycosylation level" includes a glycosylation profile/level of a recombinant protein (for example a therapeutic protein or antibody) that is modulated as compared to the glycosylation profile/level of that same protein produced by culturing a recombinant cell expressing that recombinant protein in cell culture media which is not supplemented with a peracetyl galactose such as α- or β-2-F-peracetyl galactose. The modulated glycosylation profile/level is for instance modulation of the galactosylation profile/level in said protein. In an embodiment, the modulated glycosylation profile/level, such as the modulated galactosylation profile/level, may include overall decrease in the level of galactosylation of the protein.

The term "protein" as used herein includes peptides and polypeptides and refers to compound comprising two or more amino acid residues. A protein according to the present invention includes but is not limited to a cytokine, a growth factor, a hormone, a fusion protein, an antibody or a fragment thereof. A therapeutic protein refers to a protein that can be used or that is used in therapy.

The term "recombinant protein" means a protein produced by recombinant technics. Recombinant technics are well within the knowledge of the skilled person (see for instance Sambrook et al., 1989, and updates).

The term "antibody", and its plural form "antibodies", includes, inter alia, polyclonal antibodies, affinity-purified polyclonal antibodies, monoclonal antibodies, and antigen-binding fragments, such as F(ab')2, Fab proteolytic fragments, and single chain variable region fragments (scFvs). Genetically engineered intact antibodies or fragments, such as chimeric antibodies, scFv and Fab fragments, as well as synthetic antigen-binding peptides and polypeptides, are also included.

The term "humanized" immunoglobulin refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor" (humanization by grafting non-human CDRs onto human framework and constant regions, or by incorporating the entire non-human variable domains onto human constant regions (chimerization)). Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs and a few residues in the heavy chain constant region if modulation of the effector functions is needed, are substantially identical to corresponding parts of natural human immunoglobulin sequences. Through humanizing antibodies, biological half-life may be increased, and the potential for adverse immune reactions upon administration to humans is reduced.

The term "fully human" immunoglobulin refers to an immunoglobulin comprising both a human framework region and human CDRs. Constant regions need not be present, but if they are, they must be substantially identical to human immunoglobulin constant regions, i.e., at least about 85-90%, preferably about 95% or more identical. Hence, all parts of a fully human immunoglobulin, except possibly few residues in the heavy chain constant region if modulation of the effector functions or pharmacokinetic properties are needed, are substantially identical to corresponding parts of natural human immunoglobulin sequences. In some instances, amino acid mutations may be introduced within the CDRs, the framework regions or the constant region, in order to improve the binding affinity and/or to reduce the immunogenicity and/or to improve the biochemical/biophysical properties of the antibody.

The term "recombinant antibodies" means antibodies produced by recombinant technics. Because of the relevance of recombinant DNA techniques in the generation of antibodies, one needs not be confined to the sequences of amino acids found in natural antibodies; antibodies can be redesigned to obtain desired characteristics. The possible variations are many and range from the changing of just one or a few amino acids to the complete redesign of, for example, the variable domain or constant region. Changes in the constant region will, in general, be made in order to improve, reduce or alter characteristics, such as complement fixation (e.g. complement dependent cytotoxicity, CDC), interaction with Fc receptors, and other effector functions (e.g. antibody dependent cellular cytotoxicity, ADCC), pharmacokinetic properties (e.g. binding to the neonatal Fc receptor; FcRn). Changes in the variable domain will be made in order to improve the antigen binding characteristics. In addition to antibodies, immunoglobulins may exist in a variety of other forms including, for example, single-chain or Fv, Fab, and (Fab')2, as well as diabodies, linear antibodies, multivalent or multispecific hybrid antibodies.

The term "antibody portion" refers to a fragment of an intact or a full-length chain or antibody, usually the binding or variable region. Said portions, or fragments, should maintain at least one activity of the intact chain/antibody, i.e. they are "functional portions" or "functional fragments". Should they maintain at least one activity, they preferably maintain the target binding property. Examples of antibody portions (or antibody fragments) include, but are not limited to, "single-chain Fv", "single-chain antibodies," "Fv" or "scFv". These terms refer to antibody fragments that comprise the variable domains from both the heavy and light chains, but lack the constant regions, all within a single polypeptide chain. Generally, a single-chain antibody further comprises a polypeptide linker between the VH and VL domains which enables it to form the desired structure that would allow for antigen binding. In specific embodiments, single-chain antibodies can also be bi-specific and/or humanized.

A "Fab fragment" is comprised of one light chain and the variable and CH1 domains of one heavy chain. The heavy chain of a Fab molecule cannot form a disulfide bond with another heavy chain molecule. A "Fab' fragment" that contains one light chain and one heavy chain and contains more of the constant region, between the CH1 and CH2 domains, such that an interchain disulfide bond can be formed between two heavy chains is called a F(ab')2 molecule. A "F(ab')2" contains two light chains and two heavy chains containing a portion of the constant region between the CH1 and CH2 domains, such that an interchain disulfide bond is formed between two heavy chains. Having defined some important terms, it is now possible to focus the attention on particular embodiments of the instant invention.

Examples of known antibodies which can be produced according to the present invention include, but are not limited to, adalimumab, alemtuzumab, belimumab, bevacizumab, canakinumab, certolizumab pegol, cetuximab, denosumab, eculizumab, golimumab, infliximab, natalizumab, ofatumumab, omalizumab, pertuzumab, ranibizumab, rituximab, siltuximab, tocilizumab, trastuzumab, ustekinumab or vedolizomab.

Most naturally occurring proteins comprise carbohydrate or saccharide moieties attached to the peptide via specific linkages to a select number of amino acids along the length of the primary peptide chain. Thus, many naturally occurring peptides are termed "glycopeptides" or "glycoproteins" or are referred to as "glycosylated" proteins or peptides. The predominant sugars found on glycoproteins are fucose, galactose, glucose, mannose, N-acetylgalactosamine ("GalNAc"), N-acetylglucosamine ("GlcNAc"), xylose and sialic acid. The oligosaccharide structure attached to the peptide chain is known as a "glycan" molecule. The nature of glycans impact the tridimensional structure and the stability of the proteins on which they are attached. The glycan structures found in naturally occurring glycopeptides are divided into two main classes: "N-linked glycans" or N-linked oligosaccharides" (main form in eukaryotic cells) and "O-linked glycans" or O-linked oligosaccharides". Peptides expressed in eukaryotic cells typically comprise N-glycans. The processing of the sugar groups for N-linked glycoproteins occurs in the lumen of the endoplasmic reticulum (ER) and continues in the Golgi apparatus. These N-linked glycosylations occur on asparagine residue in the peptide primary structure, on sites containing the amino acid sequence asparagine-X-serine/threonine (X is any amino acid residue except proline and aspartic acid). Main glycans that can be found on the antibody or fragments thereof secreted by CHO cells are presented in Table 1:

TABLE 1 main glycan structures (legend: squares: GlcNAc; mid-grey circles: mannose, light-grey circles: galactose; triangles: fucose; diamond: sialic acid)

| Glycan name | Glycan structure |
|---|---|
| G0 | |
| G0F | |
| G1 | |
| G1F | |
| G1F | |

TABLE 1-continued main glycan structures (legend: squares: GlcNAc; mid-grey circles: mannose, light-grey circles: galactose; triangles: fucose; diamond: sialic acid)

| Glycan name | Glycan structure |
|---|---|
| G2F | |
| G2F sialylated | |
| Man5 | |
| Man6 | |
| Man7 | |

"Glycoform" refers to an isoform of a protein, such as an antibody or a fragment thereof, differing only in the number and/or type of attached glycans. Usually, a composition comprising a glycoprotein comprises a number of different glycoforms of said glycoprotein.

Techniques for the determination of glycan primary structure are well known in the art and are described in detail, for example, in Roth et al. (2012) or Song et al. (2014). It is routine to isolate proteins produced by a cell and to determine the structure(s) of their N-glycans. N-glycans differ with respect to the number of branches (also called "antennae") comprising sugars, as well as in the nature of said branch(es), which can include in addition to the man3GlcNac2 core structure for instance N-acetylglucosamine, galactose, N-acetylgalactosamine, N-acetylneuraminic acid, fucose and/or sialic acid. For a review of standard glycobiology nomenclature see Essentials of Glycobiology, 1999.

Galactosylated proteins comprise at least one residue of galactose and include for instance glycans such as G1, G1F and/or G2F (see above Table 1).

The N-glycans structures on proteins comprise at least three residues of mannose. These structures can be further mannosylated. The mannosylated glycans such as Man5, Man6 or Man7 are called high-mannose glycans (see above Table 1).

The term "subject" is intended to include (but not limited to) mammals such as humans, dogs, cows, horses, sheep, goats, cats, mice, rabbits, or rats. More preferably, the subject is a human.

The present invention provides methods and compositions for modulating the glycosylation profile, such as modulating the galactosylation profile, of a recombinant protein such as therapeutic protein or antibody. The present invention is based on the optimization of cell culture conditions for protein manufacturing, such as production of antibodies or antigen-binding fragments, resulting in the production of a recombinant protein with modulated glycosylation profiles, preferably with decreased galactosylation.

It was observed that under cell culture conditions supplemented with a galactose analog, more particularly with a peracetyl galactose (such as a Fluorinated peracetyl galactose), the galactosylated glycoform content of the recombinant protein decreased. Thus during the cell culture production run, when it is desirable to modulate glycosylation profile of a recombinant protein, such as a galactosylation level in the recombinant protein being produced, the cell culture can be supplemented with a peracetyl galactose, such as α- or β-2-F-peracetyl galactose or can be fed with a feed medium containing a peracetyl galactose, such as α- or β-2-F-peracetyl galactose. Alternatively, the cell culture medium can already comprise said peracetyl galactose. It was also observed that under cell culture conditions supplemented with a peracetyl galactose, cell growth, viability and titer were not impacted (i.e. maintained in the range of +/−10% compared to cell grown without peracetyl galactose; it is noted that such cells grown without peracetyl galactose correspond to the control according to the present invention).

2-F-peracetyl galactose (peracetyl galactose with one fluorine atom; α/β-D-galactopyranose, 2-deoxy-2-fluoro-,1, 3,4,6-tetraacetate; alternatively herein α- or β-2F-pGal)

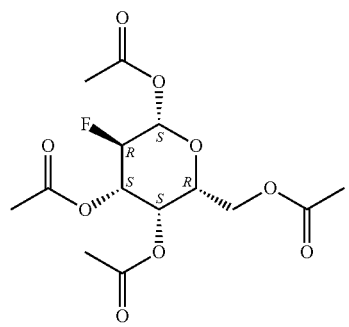

In one aspect the invention provides a method of producing a recombinant protein with a modulated glycosylation profile, such as a modulated galactosylation profile, said method comprising culturing a recombinant cell expressing said protein in cell culture medium comprising or supplemented with a peracetyl galactose. The preferred peracetyl galactose compounds are α-2-F-peracetyl galactose or β-2-F-peracetyl galactose.

Alternatively, the present invention describes a method of producing a recombinant protein with a modulated glycosylation profile, such as a modulated galactosylation profile, said method comprising culturing a host cell expressing said protein in cell culture medium complemented with at least one feed comprising a peracetyl galactose. The preferred peracetyl galactose compounds are α-2-F-peracetyl galactose or β-2-F-peracetyl galactose.

In an embodiment, here is provided the use of a peracetyl galactose in a cell culture medium or in a feed medium for modulating the glycosylation profile (e.g. modulating the galactosylation profile) of recombinant proteins produced in mammalian cells. The preferred peracetyl galactose compounds are α-2-F-peracetyl galactose or β-2-F-peracetyl galactose.

In a further aspect the invention provides a composition comprising a cell culture medium or a feed medium comprising a peracetyl galactose. The preferred peracetyl galactose compounds are α-2-F-peracetyl galactose or β-2-F-peracetyl galactose.

In a further aspect the invention provides use of a peracetyl galactose, such as α-2-F-peracetyl galactose or β-2-F-peracetyl galactose for modulating the glycosylation profile (e.g. modulating the galactosylation profile) of recombinant proteins produced in mammalian cells.

Preferably, in the context of the invention as a whole, the modulated glycosylation profile of the protein comprises modulation of the galactosylation profile, i.e. modulation of the galactosylation level in said protein. In particular, the modulation of the galactosylation level is a decrease in the overall galactosylation level in the recombinant protein, compared to a control (i.e. cells grown without peracetyl galactose). More particularly the decrease in galactosylation level is due at least to a decrease in both G1F and G2F forms. Preferably, the overall galactosylation level is decreased by about 5% to about 75% such as about 5%, 7.5%, 10%, 15%, 20%, 25%, 30%, 35%, 40%, 45%, 50%, 55%, 60%, 65%, 70% and 75% compared to the control (relative change). Should the galactosyl residues completely disappear or be close to zero (i.e. overall galactosylation level is decreased by more than 75% and up to 100%, the protein will be agalactosylated. As per the definition section, the modulation of the glycosylation level (such as the galactosylation level) or the decrease in galactosylation level is expressed in relation to the glycosylation level or the galactosylation level of the same protein produced by culturing a recombinant cell expressing said recombinant protein in cell culture media which is not supplemented with a peracetyl galactose.

The recombinant protein to be produced, in the context of the present invention as a whole, can be a therapeutic protein, an antibody or antigen binding fragment thereof, such as a human antibody or antigen-binding portion thereof, a humanized antibody or antigen-binding portion thereof, a chimeric antibody or antigen-binding portion thereof. Preferably, it is an antibody or antigen binding fragment thereof.

The methods of the present invention can be used to produce a protein, such as an antibody, having decreased amounts or levels of galactosyl residues. Modulating the galactosyl level of an antibody may indeed be needed to reach, or to maintain, a certain CDC and/or ADCC level for instance.

In the context of the invention as a whole, the peracetyl galactose compound, such as α-2-F-peracetyl galactose or β-2-F-peracetyl galactose, is preferably added in a cell culture medium at a concentration before seeding (i.e. before inoculation) of or of about 0.1 to 200 µM, preferably of or of about 1 to 120 µM, even preferably of or of about 20 to 100 µM such as at concentration of or of about 20, 25, 30, 35, 40, 45, 50, 60, 65, 70, 80, 90 or 100 µM. For example, by adjusting the concentration of a peracetyl galactose compound the galactosylation profile can be modulated. Alternatively, should the peracetyl galactose compound be added to a cell culture medium (as a supplement or as a feed) after seeding, the dilution factor linked to the inoculation itself has to be taken into account. By knowing the culture medium volume before inoculation and the volume of the cell culture at the time the supplementation is made (or the volume of inoculum added to the culture medium before seeding), it is easy to retrieve the dilution factor. Said dilution factor is typically ranged from 10 to 15%. However, it can be up to 20% or even higher in case the cells grow less in the expansion phase. For instance, should one targets the equivalent of 60 µM before seeding and the dilution factor being of 10% or 20%, the peracetyl galactose compound will have to be added at a final concentration (once in the inoculated culture) of respectively 54 or 48 µM. Typically, and considering a dilution factor ranged between 10 and 20%, should the peracetyl galactose compound be added to a cell culture medium (as a supplement or as a feed) after seeding, its final concentration once in the culture medium will be of or of about 0.08 and 180 µM, even preferably of or of about 0.4 to 108 µM. This final concentration has to be understood as the final concentration for the given supplement/feed. Indeed, and as an example, the skilled person will understand that should the peracetyl galactose compound be added during culture in 2 feeds, the total final concentration will correspond to the final concentration of the second supplement/feed, added to the remaining final concentration of the first supplement/feed.

For the purposes of this invention, cell culture medium is a medium suitable for growth of animal cells, such as mammalian cells, in in vitro cell culture. Cell culture media formulations are well known in the art. Cell culture media may be supplemented with additional components such as sugars, vitamins, hormones, and growth factors, depending on the needs of the cells in culture. Preferably, the cell culture media are free of animal components; they can be serum-free and/or protein-free. In certain embodiments of the present invention, the cell culture medium is supplemented with the peracetyl galactose, for example, at the start of culture, and/or in a fed-batch or in a continuous manner. The addition of the peracetyl galactose supplement may be based on measured intermediate glycosylation profiles (e.g. intermediate galactosylation profiles/levels). Said addition during culture can be done via a feed consisting only of peracetyl galactose compound or via a feed comprising the supplement of peracetyl galactose compound among other components.

In an embodiment of the present invention, the host cell is preferably a mammalian host cell (herein also refer to as a mammalian cell) including, but not limited to, HeLa, Cos, 3T3, myeloma cell lines (for instance NS0, SP2/0), and Chinese hamster ovary (CHO) cells. In a preferred embodiment, the host cell is Chinese Hamster Ovary (CHO) cells, such as CHO-S cell and CHO-k1 cell.

In the context of the invention as a whole, the recombinant cell, preferably mammalian cell, is grown in a culture system such as a bioreactor. The bioreactor is inoculated with viable cells in a culture medium comprising or supplemented with a peracetyl galactose. Preferably the culture medium is serum-free and/or protein-free. Once inoculated into the production bioreactor the recombinant cells undergo an exponential growth phase. The growth phase can be maintained using a fed-batch process with bolus feeds of a feed medium optionally supplemented with said peracetyl galactose or of a feed consisting of peracetyl galactose. Preferably the feed medium is serum-free and/or protein-free. These supplemental bolus feeds typically begin shortly after the cells are inoculated into the bioreactor, at a time when it is anticipated or determined that the cell culture needs feeding. For example, supplemental feeds can begin on or about day 3, 4 or 5 after the start of the culture or a day or two earlier or later. The culture may receive two, three, or more bolus feeds during the growth and production phases. Any one of these bolus feeds can optionally be supplemented with the peracetyl galactose. The supplementation or the feed with the peracetyl galactose can be done at the start of the culture, in fed-batch, and/or in continuous manner. Alternatively, the supplementation with peracetyl galactose can be performed only after the start of the culture: in such a case peracetyl galactose will not be added in the culture medium at the start of the culture (e.g. at the time of inoculation). When peracetyl galactose (such as α-2-F-peracetyl galactose or β-2-F-peracetyl galactose) is added as a feed, it can be supplemented separately (as a single component feed) or together with the usual supplemental feed (as part of another type of feed). Said feed of peracetyl galactose can begin on or about day 3, 4 or 5 after the start of the culture or a day or two earlier or later. The culture may receive two, three, or more bolus feeds during the growth and production phases. For instance, but not to be seen as limiting examples, 1) a first feed of peracetyl galactose can be added on day 3, followed by additional peracetyl galactose feeds on days 5, 7 and 10 or 2) a first feed of peracetyl galactose can be added on day 5, followed by additional peracetyl galactose feeds on days 7 and 10.

The methods, compositions and uses according to the present invention may be used to improve the production of recombinant proteins in multistep culture processes. In a multiple stage process, cells are cultured in two or more distinct phases. For example cells are cultured first in one or more growth phases, under conditions improving cell proliferation and viability, then transferred to production phase(s), under conditions improving protein production. In a multistep culture process, some conditions may change from one step (or one phase) to the other: media composition, shift of pH, shift of temperature, etc. The growth phase can be performed at a temperature higher than in production phase. For example, the growth phase can be performed at a first temperature from about 35° C. to about 38° C., and then the temperature is shifted for the production phase to a second temperature from about 29° C. to about 37° C. The cell cultures can be maintained in production phase for days or even weeks before harvest.

The cell lines (also referred to as "recombinant cells") used in the invention are genetically engineered to express a protein of commercial or scientific interest. Methods and vectors for genetically engineering of cells and/or cell lines to express a polypeptide of interest are well known to those of skill in the art; for example, various techniques are illustrated in Ausubel et al. (1988, and updates) or Sambrook et al. (1989, and updates). The methods of the invention can be used to culture cells that express recombinant proteins of interest. The recombinant proteins are usually secreted into the culture medium from which they can be recovered. The recovered proteins can then be purified, or partially purified using known processes and products available from commercial vendors. The purified proteins can then be formulated as pharmaceutical compositions. Suitable formulations for pharmaceutical compositions include those described in Remington's Pharmaceutical Sciences, 1995.

In a further aspect, the invention provides a composition comprising a recombinant protein with a modulated glycosylation profile (e.g. a modulated galactosylation profile) produced by the methods of the invention.

The compositions of the invention comprising a recombinant protein with a modulated glycosylation profile, for example an antibody or antigen-binding fragment thereof, with a decreased galactosylation level or amount, may be used to treat any disorder in a subject for which the therapeutic protein (such as an antibody or an antigen binding fragment thereof) comprised in the composition is appropriate for.

In a further aspect, the invention provides a pharmaceutical composition comprising the recombinant protein with a modulated glycosylation profile (e.g. modulated galactosylation profile) produced by the methods of the invention and a pharmaceutically acceptable carrier. The recombinant protein is preferably a therapeutic protein, and can be an antibody or antigen binding fragment thereof, such as a human antibody or antigen-binding portion thereof, a humanized antibody or antigen-binding portion thereof, a chimeric antibody or antigen-binding portion thereof. Preferably, it is an antibody or antigen binding fragment thereof, with a decreased galactosylation level or amount compared to the same antibody or antigen binding fragment thereof produced in absence of supplementation in peracetyl galactose.

In certain embodiments, the pharmaceutical compositions of the invention comprising a recombinant protein with a modulated glycosylation profile may be formulated with a pharmaceutically acceptable carrier as pharmaceutical (therapeutic) compositions, and may be administered by a variety of methods known in the art (see for instance Remington's Pharmaceutical Sciences, 1995). Such pharmaceutical compositions may comprise any one of salts, buffering agents, surfactants, solubilizers, polyols, amino acids, preservatives, compatible carriers, optionally other therapeutic agents, and combinations thereof. The pharmaceutical compositions of the invention comprising a recombinant protein with a modulated glycosylation profile, are present in a form known in the art and acceptable for therapeutic uses, such as liquid formulation, or lyophilized formulation. Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features.

The present disclosure is therefore to be considered as in all aspects illustrated and not limiting the scope of the invention being indicated by the appended Claims, and all changes which come within the meaning and range of equivalency are intended to be embraced therein.

The foregoing description will be more fully understood with reference to the following examples. Such Examples, are, however, exemplary of methods of practising the present invention and are not intended to limit the scope of the invention.

EXAMPLES

Material and Methods

I. Cells, Cell Expansion and Cell Growth

1) Cells

First assays were performed with an antibody produced in a CHO cell line: CHO-S cells expressing IgG1 mAb1, herein "Cells mAb1" or "mAb1 cells". "mAb1" is a fully human monoclonal antibody directed against a soluble protein. Its isoelectric point (pI) is about 8.20-8.30.

Additional assays were performed with another antibody also produced in another CHO cell line: CHO-Ki cells expressing IgG1 mAb2, herein "Cells mAb2" or "mAb2 cells". "mAb2" is a humanized monoclonal antibody directed against a receptor found on the cell membrane. Its isoelectric point (pI) is about 9.30.

2) Cell Expansion

Cell expansion was performed in tubes in a medium suitable for cell expansion. Assays in fed-batch started after at least one week expansion.

3) Inoculation

Cells expressing mAb1 were inoculated at $0.3 \times 10^6$ cells per millilitre (mL), whereas Cells expressing mAb2 were inoculated at $0.2 \times 10^6$ cells per millilitre (mL).

4) Fed-Batch

All assays were performed in fed-batch culture.

For examples 1-3: A serum-free chemically defined culture medium was used. It was used as it is, or it was supplemented with α- or β-2-F-peracetyl galactose (herein α- or β-2F-pGal; Biosynth & AX Molecules) at different concentrations (0-200 μM before seeding). The concentrations indicated on FIGS. 1, 2, 3 and 4 are the concentrations in α- or β-2F-pGal in the culture medium at day 0, just before the inoculation. The culture medium was fed, on a regular basis, with a chemically defined feed medium, as well as with glucose in order to keep said glucose level in the range of >0 to about 8 g/L (feeds are done at days 3, 5, 7, 10 and 12).

For example 4: Additional experiments were run in similar conditions, except with regard to supplementation with α- or β-2-F-peracetyl galactose. In such a case, a serum-free chemically defined culture medium was used, supplemented with α- or β-2-F-peracetyl galactose as mentioned thereafter in Table 2.

The cultures were performed in deepwell plates (DWP) with a working volume of 450 μL. They were incubated at 36.5° C., 5% de $CO_2$, 90% humidity and shaken at 320 rpm. Each of the fed-batch culture lasted 14 days. It is well known that experiments in DWP are artificial, although they allow a first screening of culture conditions. In order to confirm that the results obtained in DWP were reproducible at higher scale, similar experiments were also run in TubeSpin® (also called herein shake tubes or ST), with a working volume of 30 mL cell culture (same culture condition than for deepwell plates).

TABLE 2

Experimental conditions for example 4

| Experiment | Day 3 | Day 5 | Day 7 | Day 10 |
|---|---|---|---|---|
| β-2F-pGal-d3 | ✓ | ✓ | ✓ | ✓ |
| β-2F-pGal-d5 | — | ✓ | ✓ | ✓ |
| β-2F-pGal-d7 | — | — | ✓ | ✓ |

II. Analytical Methods

For DWP experiments, viable cell density and viability were measured with the Guava easyCyte® flow cytometer. Antibody titers were measured with the fortéBIO Octet®.

For TubeSpin® experiments, viable cell density and viability were measured with the ViCell®. Antibody titers were measured using Biacore®.

Glycosylation profiles were established by capillary gel electrophoresis with laser-induced fluorescence (CGE-LIF; for DWP and for Shake tubes experiments) or by Ultra Performance Liquid Chromatography-2-amino-benzamide labelling technique (2AB-UPLC; for Shake tubes experiments). Groups of glycans were defined as thereafter in Table 3.

TABLE 3

Main groups of glycans identified (legend: squares: GlcNAc; mid-grey circles: mannose, light-grey circles: galactose; triangles: fucose)

| Group name | Composition |
|---|---|
| G0 | |
| G0F | |
| G1 | |
| G1F | and |
| G2F | |
| Non-Fuc | Non-fucosylated glycans |
| Fuc | Fucosylated glycans |
| Gal | Galactosylated glycans |
| Man | High mannose glycans |

Example 1—Impact of 2-F-Peracetyl Galactose on mAb1 Antibody—in DWP

The cells were cultivated and the results analysed as disclosed in the material and method section. It is noted that the controls (or control conditions) according to the present invention correspond to cells grown without peracetyl galactose.

Figure 1:
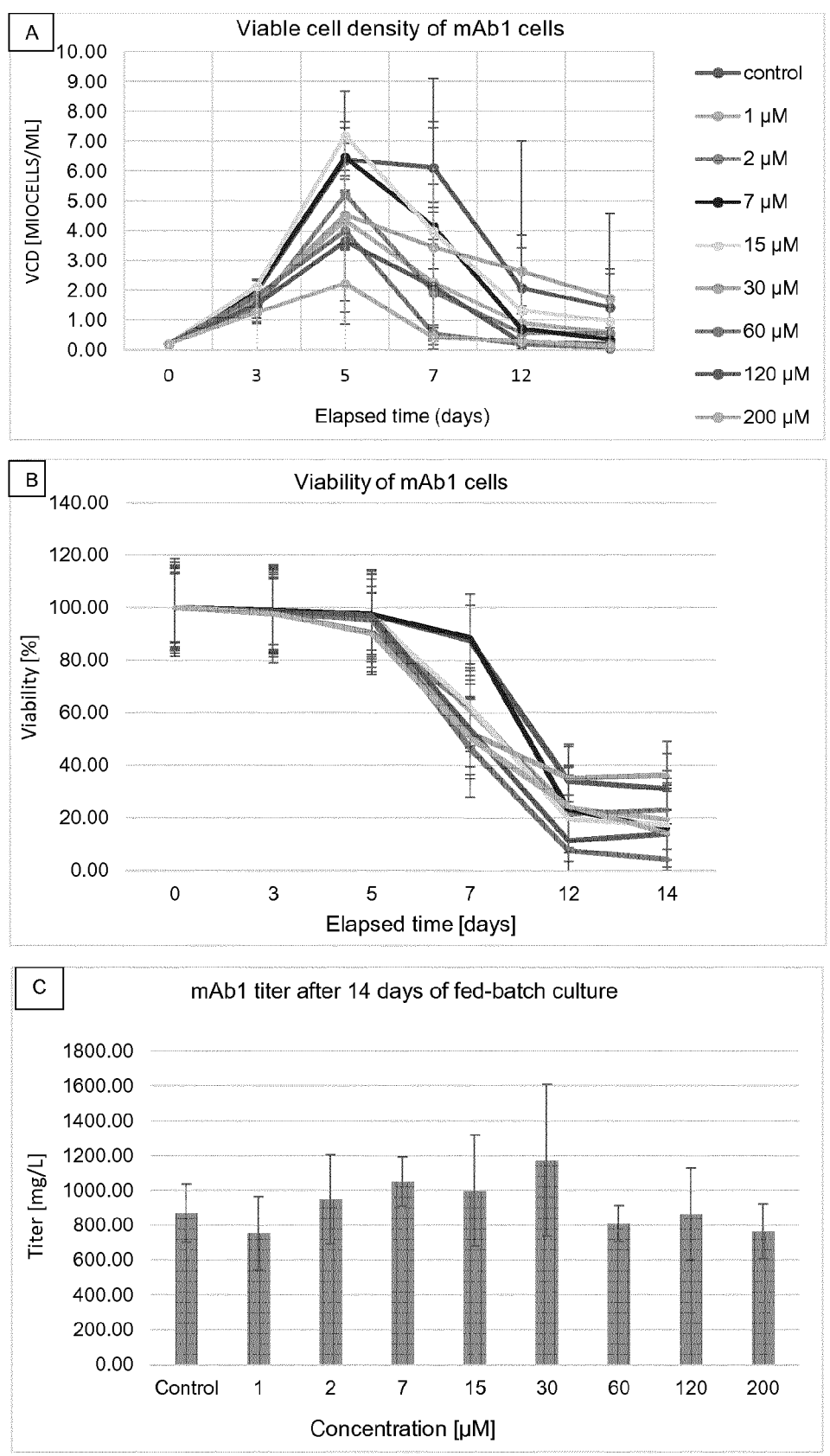
FIG. 1 shows density of viable cells (FIG. 1A; Guava®) and viability (FIG. 1B; Guava®) in relation to time as well as titer on day 14 (FIG. 1C; Octet®) for mAb1 cells cultured at different α-2F-pGal concentrations in microplates (DWP). Results are presented as mean±standard deviation. The legend for FIG. 1A also applies to FIG. 1B. The concentrations which are mentioned refer to the concentrations at day 0, just after the inoculation.
Figure 2:
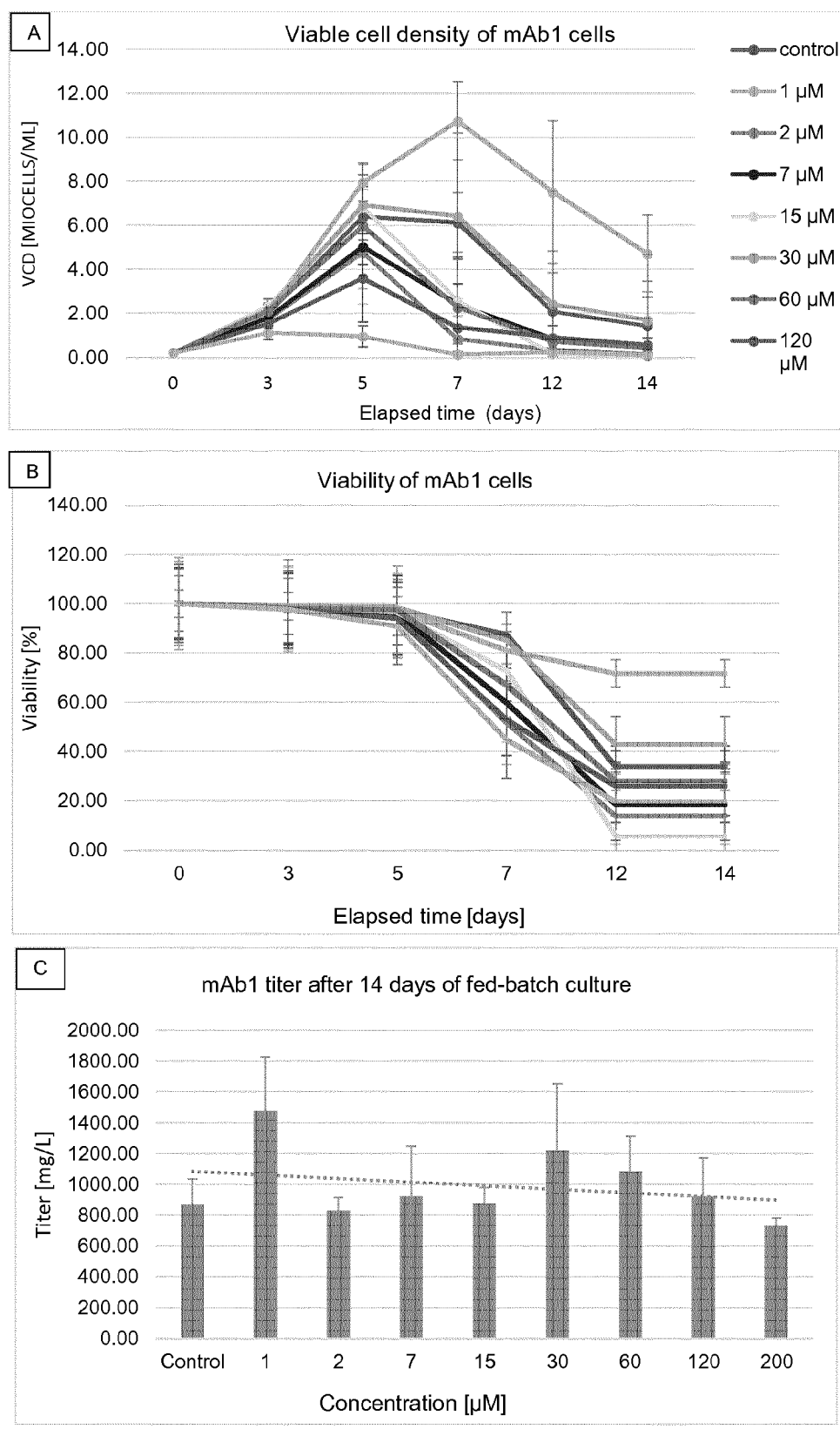
FIG. 2 shows density of viable cells (FIG. 2A; Guava®) and viability (FIG. 2B; Guava®) in relation to time as well as titer on day 14 (FIG. 2C; Octet®) for mAb1 cells cultured at different β-2F-pGal concentrations in microplates (DWP). Results are presented as mean±standard deviation. The legend for FIG. 2A also applies to FIG. 2B. The concentrations which are mentioned refer to the concentrations at day 0, just after the inoculation.

Viable Cell Density and Viability:

Viable cell density and viability as a function of elapsed time, as well as antibody titer at the end of the fed-batch culture are shown on FIG. 1 (for α-2F-pGal) and FIG. 2 (for β-2F-pGal). At concentrations up to 30 μM, both α- and β-2F-pGal have no impact on cell growth until the end of culture (FIGS. 1A and 1B; FIGS. 2A and 2B). At concentrations of about 60 μM and higher, the two compounds have a negative impact on cell growth. In parallel, at concentrations up to 60 μM, one cannot distinguish a titer trend either at day 10 (data not shown) or day 14 (FIGS. 1C and 2C). As shown in FIGS. 1C and 2C, at 2F-pGal media concentration up to 60 μM, protein titer stays above the protein titer of the control at day 10 and day 14. At 60 μM, the decrease of growth cell does not have a real impact on titer. However, at higher concentration, decrease of number of cells is reflected on titers, which decrease by about 1.2 factor comparing to control. Impact on growth and titers is considered acceptable until about 60 μM for this antibody.

Figure 3:
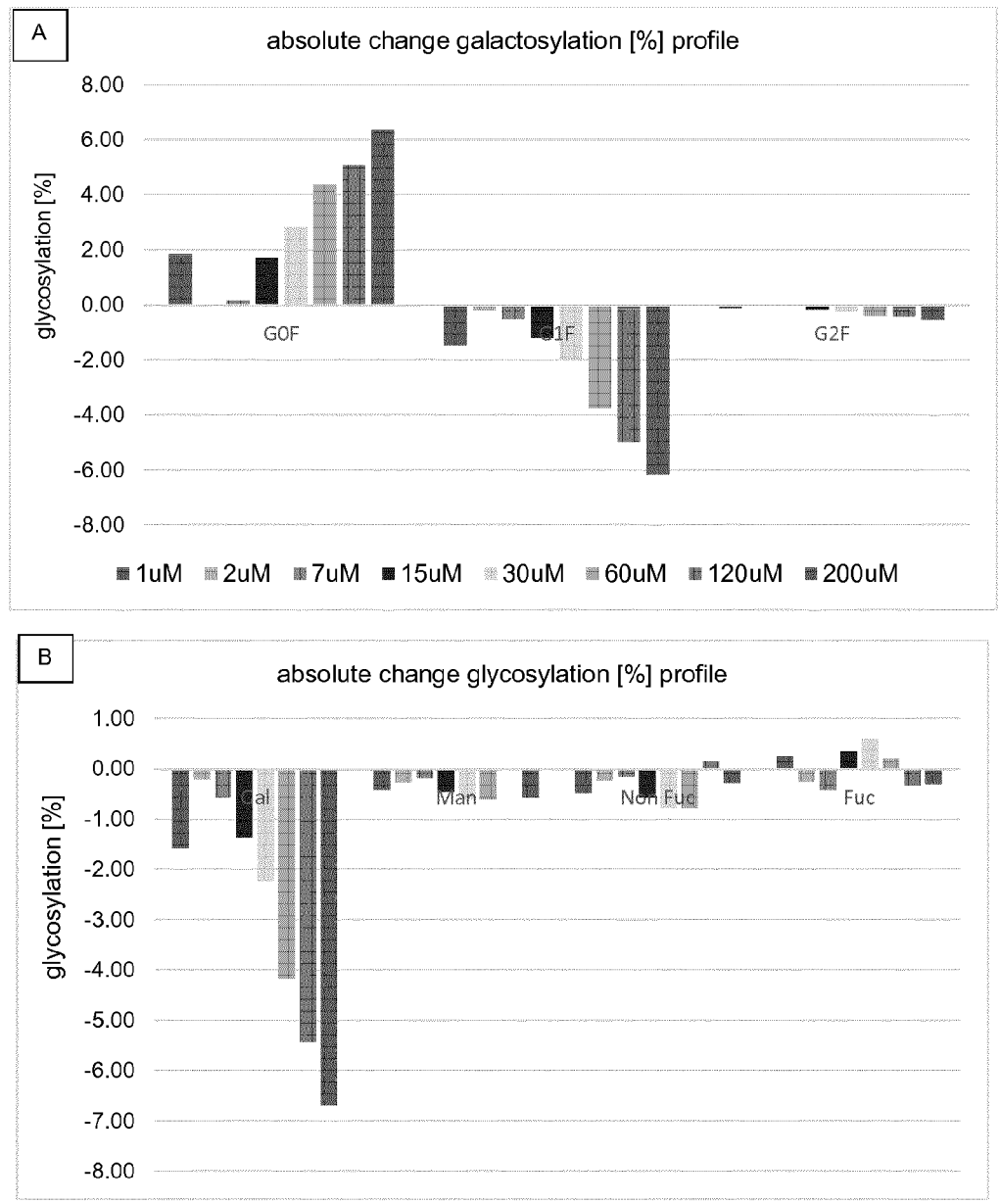
FIG. 3 shows the absolute change in galactosylation profile compared to control according to β-2F-pGal media concentration (FIG. 3A); as well as the absolute change in glycosylation profile compared to control according to β-2F-pGal media concentration (FIG. 3B).

Glycosylation Profiles:

Glycosylation profiles obtained by CGE-LIF analysis are shown on FIG. 3 (FIGS. 3A and 3B for β-2F-pGal). The data obtained underline that both α- and β-2F-pGal are able to modulate the glycosylation of an antibody, and in particular are able to decrease galactosylated glycans, without impacting mannosylated, non-fucoslyated and fucosylated glycoforms. In particular, control proteins have 10% galactosylated N-oligosaccharides whereas the proteins obtained by cell cultivating in media containing 30, 60, 120 and 200 μM α-2F-pGal, respectively contain 8.3, 6.8, 6.0 and 4.8% galactosylated N-oligosaccharides (data not shown). The absolute change in galactosylated N-oligosaccharide compared to the control is respectively 1.3, 2.8, 3.5 and 4.8% (these changes correspond respectively to a 17%, 32%, 40% and 52% relative decrease compared to control) for 30, 60, 120 and 200 μM α-2F-pGal concentration. For G1F the absolute change in galactosylated N-oligosaccharide compared to the control is respectively 1.1, 2.5, 3.1 and 4.4%; as for G2F, the absolute change is respectively 0.2, 0.3, 0.35 and 0.4% for 30, 60, 120 and 200 μM α-2F-pGal.

Similar results were obtained with β-2F-pGal (see FIGS. 3A and 3B). Control proteins have 10.6% galactosylated N-oligosaccharides whereas the proteins produced in media containing 30, 60, 120 and 200 β-2F-pGal, respectively contain 8.3, 6.4, 5.1 and 3.9% galactosylated N-oligosaccharides (these changes correspond respectively to a 22%, 40%, 52% and 64% decrease compared to control). The absolute change in galactosylated N-oligosaccharide compared to the control is respectively 2.2, 4.2, 5.4% and 6.7% for 30, 60, 120 and 200 μM β-2F-pGal concentration. For G1F the absolute change in galactosylated N-oligosaccharide compared to the control is respectively 1.1, 2.5, 3.1 and 4.4% as for G2F, the absolute change is respectively 0.20, 0.30, 0.33 and 0.40% for 30, 60, 120 and 200 μM β-2F-pGal.

For the two compounds, absolute change compared to control is comprised within the possible analytical noise (less than 1%) with regards to mannosylated, non-fucosylated and fucosylated oligosaccharides. Hence, these quality attributes are not affected by any one of α- or β-2F-pGal.

Conclusion for mAb1 in DWP:

α- and β-2F-pGal media concentrations below 30 μM do not impact cell density, cell viability and protein titer. However, below 30 neither α- or β-2F-pGal does have a significant inhibition effect on galactosylation. Thus below 30 neither α- or β-2F-pGal is a good galactosylation inhibitor. When concentrations are higher than 30 μM, a significant inhibition effect is observed on galactosylation. Nevertheless, cell density, cell viability and protein titer can be negatively impacted, especially at concentrations higher than 60 μM. At concentrations ranged between 30 and 60 both α- and β-2F-pGal have no impact on protein titre but they impact galactosylation with relative decrease ranged from about 20% to 40%. Thus a concentration range between 30 and 60 μM seems to be the optimum concentration range taking into account the impact on cell density, cell viability, protein titer and galactosylation inhibition. Example 1 shows that any one of α- or β-2F-pGal specifically inhibits galactosylation, without any influence on mannosylation and fucosylation.

Example 2—Impact of 2-F-Peracetyl Galactose on mAb1 Antibody—in TubeSpin®

The cells were cultivated and the results analysed as disclosed in the material and method section.

Example 2.1 Preliminary Assessment

Figure 4:
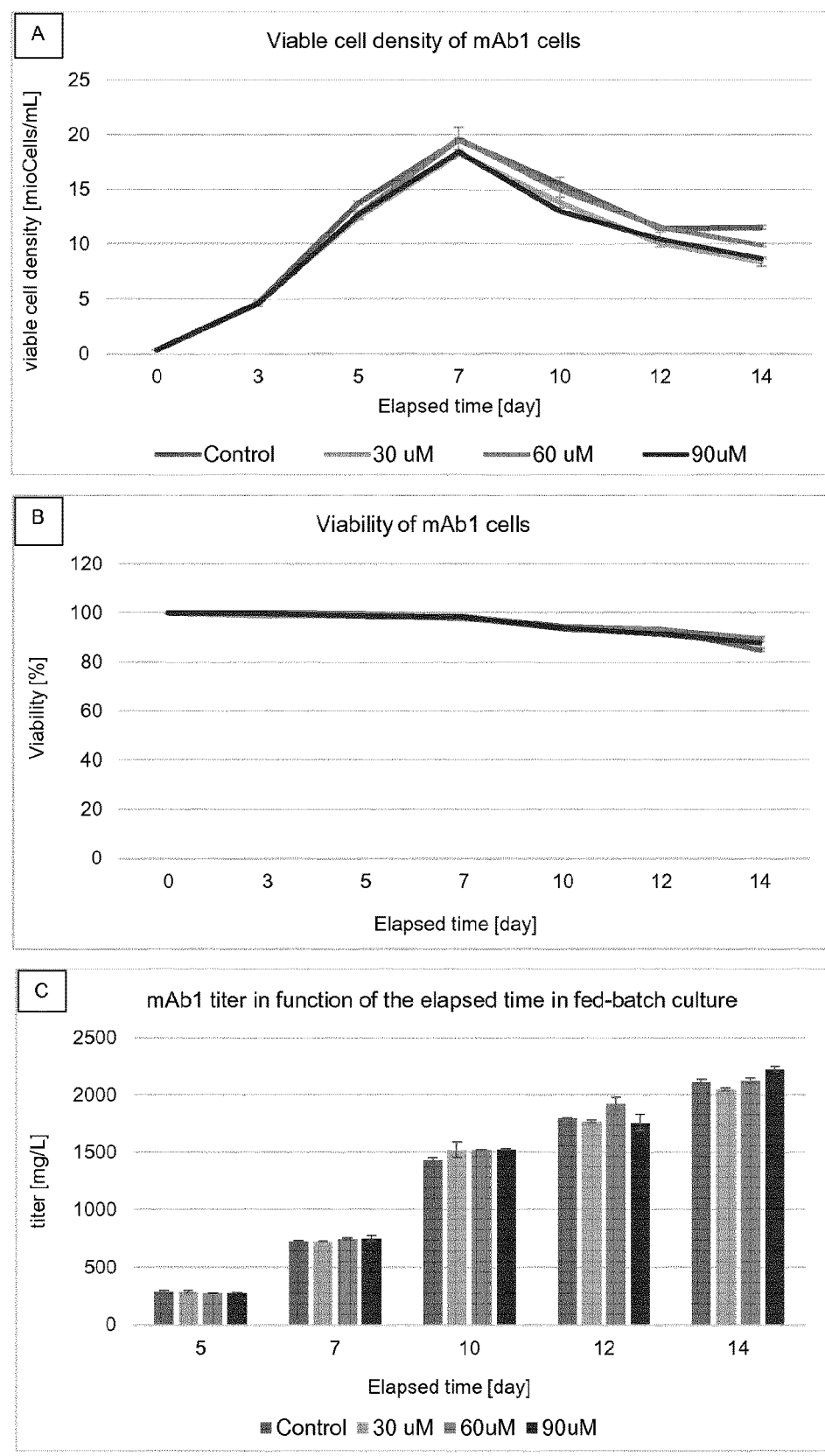
FIG. 4 shows density of viable cells (FIG. 4A; ViCell®) and viability (FIG. 4B; ViCell®) in relation to time as well as titer in relation to the elapsed time (FIG. 4C; Biacore®)

Viable Cell Density and Viability:

Viable cell density and viability as a function of elapsed time, as well as antibody titer at the end of the fed-batch culture are shown on FIG. 4 (for α-2F-pGal) and FIG. 5 (for β-2F-pGal). At any one of the concentrations tested, i.e. 30, 60 and 90 μM, α-2F-pGal has no negative impact on cell growth or protein titer until the end of culture: the values are stable compared to the control. Similar results were observed for β-2F-pGal, although only one concentration was tested (i.e. 60 μM).

Glycosylation Profiles:

Glycosylation profiles are shown on FIG. 6 (FIGS. 6A and 6B for α-2F-pGa). The data obtained confirm the results obtained in DWP: both α- and β-2F-pGal are able to modulate the glycosylation of an antibody, and in particular are able to decrease galactosylated glycans, without impacting mannosylated, non-fucoslyated and fucosylated glycoforms. From FIGS. 6A and 6B, one can see the absolute change in the glycosylation profile of the proteins produced in presence of α-2F-pGal: this results in a significant decrease of the galactosylation. For the galactosylated N-oligosaccharides the absolute change compared to the control is respectively 2.0, 4.61, 4.5% for 30, 60 and 90 μM α-2F-pGal media concentration (these changes correspond respectively to about 16%, 37% and 36% relative decrease compared to control). Concerning G1F, the absolute change compared to the control is respectively 1.9, 4.3, 4.3% for 30, 60 and 90 μM α-2F-pGal media concentration. As for G2F the absolute change compared to the control is 0.11, 0.27, 0.33% for 30, 60 and 90 μM α-2F-pGal media concentration.

Similar results were obtained with β-2F-pGal (data not shown): the absolute change in galactosylation is around 4%, at a concentration of 60 μM.

For the two compounds, absolute change compared to control is comprised within the possible analytical noise (less than 1%) with regards to mannosylated, non-fucosylated and fucosylated oligosaccharides, also confirming the results obtained in DWP.

Example 2.2. Confirmatory Assessment

Viable Cell Density and Viability:

FIG. 7A shows the viable cell density of cell line 1 cultures at 30, 60 and 90 µM α-2F-p-galactose in the medium. The control culture reached the highest density on day 7, climbing up to $19.5 \times 10^6$ viable cells/mL. The α-galactose analog supplementation exhibited no growth inhibitory effect in the first part of the culture. Nonetheless, cell densities were slightly lower from day 10 until the end of the culture for concentrations in α-galactose analogs at concentrations of 30 and 90 µM. On day 14, the control cultures were harvested at a density of $11.5 \times 10^6$ viable cells/mL. The supplemented cultures were in the range of 8.4 to $9.9 \times 10^6$ viable cells/mL. Experiments with 60 µM β-2F-peracetyl-galactose peaked lower, at day 7, at $12.8 \times 10^6$ viable cells/mL. The data points before however comparable to the control.

Viabilities were comparable on day 7 for all of the culture conditions (FIG. 7B). It is therefore possible that the difference observed in FIG. 7A was rather due to an analytical artefact, stemming from the imaged based cell fluorescent analyzer. This hypothesis is further supported by the fact that protein concentrations in the supernatant of the β-2F-p-galactose containing cultures were comparable to the control at culture days 5, 7, 10, 12 and 14 (yielding 2225 mg/L at day 14). Likewise, the product titers (FIG. 7C) of the -α-galactose analog were comparable at all time points, attaining at the end of the culture 2115, 2050 and 2130, 2225 mg/L, respectively, in the control, at 30, 60 and 90 µM. No detrimental effect on cell culture performance was observed in the entire concentration range between 0 and 90 µM α-2F-p-galactose and at 60 µM β-2F-p-galactose.

Glycosylation Profiles:

According to FIG. 8B, the galactosylation inhibiting effects of the galactose analog observed in 96-DWP were confirmed in shake tubes. The total level of galactosylation decreased by 2.0, 4.6 and −4.5% at respectively 30, 60 and 90 µM α-2F-peracetyl-galactose and by −5.0 with 60 µM β-2F-peracetyl-galactose. The monogalactosylated form changed by −1.9, −4.3, −4.3% at respectively 30, 60 and 90 µM α-2F-peracetyl-galactose and by −4.7% in the presence of the β-analog. The entirely galactosylated glycoform slightly decreased between −0.1 and −0.3%. Overall, the performance of the two anomers was comparable. The use of 2F-p-galactose is worthwhile due to its high specificity which limits the effect on other glycan species.

Conclusion for mAb1 in TubeSpin®:

Compared to 96 DWP platform, using a spin tube platform leads to more stable results concerning cell density, cell viability and protein titer regardless of the α- and β-2-F-peracetyl-galactose media concentration (tested ranges: between 30 and 90 µM). Galactosylation inhibition is significant with an absolute change of about 2 and 4.5% for a α-2F-pGal media concentration respectively of 30 and 60 µM. Thus a concentration range between 30 and 60 µM seems to be the optimum concentration range taking into account the impact on cell density, cell viability, protein titer and galactosylation inhibition, as the absolute change in galactosylation for a α-2F-pGal media concentration of 90 µM stays the same as the one for 60 µM. The same is observed with β-2F-pGal addition.

Example 2 confirms that α- and β-2F-pGal specifically inhibit galactosylation, without any influence on mannosylation and fucosylation.

Example 3—Impact of 2-F-Peracetyl Galactose on mAb2 Antibody—in TubeSpin®

The cells were cultivated and the results analysed as disclosed in the material and method section.

Viable Cell Density and Viability:

As FIG. 9A highlights, the overall viable cell densities of the 30 and 60 µM α-2F-p-galactose cultures were comparable to the control, which reached a maximum cell density of 11.2×106 viable cells/mL on day 7. A level of 90 µM led to a slight reduced cell growth, peaking at 10.0×106 viable cells/mL. The viabilities of the entire supplement concentration range were comparable to the control condition (FIG. 9B)(about 97% cell viability at day 7). Intermediated concentrations (30 and 60 µM) kept the productivity globally unchanged (FIG. 9C). For instance at day 7, the titer is around 730 mg/L for the control and 720 mg/L for both 30 and 60 µM of α-2F-p-galactose. Similarly, at day 14, the titer is around 3300 mg/L for the control, around 3400-3420 mg/L for both 30 and 60 µM of α-2F-p-galactose. The highest inhibitor concentration entailed a little titer reduction, although deemed not significant (e.g.: about 670 mg/L at day 7 or 3200 mg/L at day 14.

Glycosylation Profiles:

FIG. 10A shows the absolute glycan change in function of the α-2F-peracetyl-galactose concentration in the medium. Like for cell line 1, the galactose analog reduced galactosylation. The reduction amounted to −0.95, −2.05 and −1.4% at respectively 30, 60 and 90 µM (absolute change). Its presence also had a non negligible effect on the overall fucosylated species (+0.5%). FIG. 10B zooming in the individual terminal galactose species displays a −0.85, −1.85 and −1.2% decrease for FA2G1 and small change of the FA2G2 abundance of −0.09, −0.19 and −0.19% at respectively 30, 60 and 90 µM. One should keep in mind that 2AB-UPLC rather than CGE-LIF was used to quantity the glycan pattern of cell line 2 cultures.

Conclusion for mAb1 and mAb2 in Shake Tubes:

Example 3 confirms that α- and β-2F-pGal specifically inhibit galactosylation, without any influence on mannosylation and fucosylation, whatever the antibody (here, shown with mAb1 and mAb2) and the cell line (here, shown with cell mAb1 and cell mAb2).

Example 4—Impact of 2-F-Peracetyl Galactose on mAb1 Antibody—Supplementation as Feed after the Start of the Culture Viable Cell Density and Viability:

Rather than supplementing the medium prior to inoculation, it was decided to start the galactose analog addition on day 3, 5 or 7 (respectively β-2F-pGal-d3, β-2F-pGal-d5 and β-2F-pGal-d7; see Table 2). Cell line 1 was used for these experiments. FIG. 11A shows how β-2F-p-galactose affected the viable cell density in function of the addition time. The peak cell densities were reached on day 7. No significant difference between the control and the β-2F-pGal-d3 supplemented cultures was observed. They both levelled off at 20.8 and 21.2×106 viable cells/mL, respectively. The feed on day 5 reduced the maximum cell density, reaching 18.6×106 viable cells/mL. Overall, it can be assumed that the presence of β-2F-p-galactose induced limited changes on cell growth until day 7. In the second half of the culture, both the cell density and the viability (FIG. 11B) are correlated with the feed timing. Supplementation on day 3 most strongly impacted the course of the culture. At harvest, the cell density amounted to 9.8×106 viable cells/mL (control: 11.8×106 viable cells/mL). The viability dropped notably faster than in the control, falling below 60%. Feed addition on day 5 and 7, respectively, entailed viabilities on day 14 of 78 and 90% (control: 93%). According to FIG. 11C, no clear titer trend came forward. Early supplementation induced a slight titer increase on days 7 and 10, but then reduced productivity at later stages of the culture. While the control yielded 2870 mg/L, supplementation on day 3 (β-2F-pGal-d3), 2560 mg/L. The addition of β-2F-p-galactose on day 5 (—(3-2F-pGal-d5) favored antibody expression, producing 3215 mg/L. Addition on day 7 (—(3-2F-pGal-d7), resulted in a considerably lower protein titer: 2100 mg/L. In comparison to media supplementation, introducing β-2F-p-galactose by means of feeding, limits detrimental effects on the cell performance. Even when starting the feed on day 7, the final additive concentration in the supernatant was considerably higher than in media supplementation, where important growth and productivity reduction resulted as mentioned previously.

Glycosylation Profiles:

Feed optimization, using β-2F-p-galactose resulted in an important inhibition of galactosylated glycoforms as shown in FIG. 12A. 11.5% of the secreted antibodies in the control were galactosylated. Feed addition from day 3 (—(3-2F-pGal-d3) resulted in the strongest inhibition: overall galactosylation decreased by −8.5%. Conditions starting the feed on day 5 (—(3-2F-pGal-d5) and 7 (β-2F-pGal-d7) brought about reductions of −7.0 and −4.6%, respectively. Like in the medium supplementation experiments (at the start of the culture), β-2F-p-galactose specifically target galactosylation. Effects on the other glycan species remained small. The mono-galactosylated species dropped by −8.0, −6.7 and −4.4%, while the di-galactosylated entity decreased by −0.41, −0.33 and −0.19 when starting the feed on day 3, 5 and 7, respectively (FIG. 12B). The amplitude of the galactosylation inhibition was correlated with the start date of the supplement feed, and thus, the level of -2F-p-galactose in the supernatant.

Conclusion of Example 4

Feed optimization proofed to be an excellent strategy to further enhance the effect of the supplement. Furthermore, feed supplementation allowed to increase the total amount of the additive, entailing considerably smaller detrimental effects on cell culture performance in comparison with medium supplementation.

Overall Conclusions

The present examples demonstrate that α- and β-2F-pGal specifically inhibit galactosylation, without influence on mannosylation and fucosylation. The skilled person will understand from the results of the above examples that he can use any one of α- and β-2F-pGal for modulating the galactosylation profile of any antibodies and any proteins, whatever the cell line that is used for production, and in particular to decrease the overall galactosylation level. Feed optimization proofed to be an excellent strategy to further enhance the effect of the supplement.

The exact concentration of α- and β-2F-pGal to be added in the cell culture media, as well as the timing for supplementation (either at the start of the culture, as for instance shown in examples 1 to 3, or as a feed at later points in time, as shown for instance in example 4) will have to be determined case by case, depending on the galactosylation profile the skilled one wish to obtain molecule per molecule. This determination can be done without involving any inventive skill, based on the teaching of the present invention. The skilled person will also understand that he can use α- or β-2F-pGal in any method for producing a protein such as an antibody, even if he does not aim to reach a particular glycosylation profile.

REFERENCES

1) Eon-Duval et al., 2012. Quality Attributes of Recombinant Therapeutic Proteins: An Assessment of Impact on Safety and Efficacy as Part of a Quality by Design Development Approach. Biotechnol. Prog. 28(3): 608-622.
2) N. Yamane-Ohnuki et M. Satoh, 2009. Production of therapeutic antibodies with controlled fucosylation; mAbs, 1(3): 230-236.
3) Yu et al., 2012. Characterization and pharmacokinetic properties of antibodies with N-linked Mannose-5 glycans"; mAbs, 4(4):475-487.
4) Hodoniczky J, Zheng Y Z, James D C. Control of recombinant monoclonal antibody effector functions by Fc N-glycan remodeling in vitro. Biotechnol Prog. 2005; 21:1644-52.
5) Ziv Roth et al., 2012. Identification and Quantification of Protein Glycosylation; International Journal of Carbohydrate Chemistry, Article ID 640923.
6) Ting Song et al., 2014. In-Depth Method for the Characterization of Glycosylation in Manufactured Recombinant Monoclonal Antibody Drugs; *Anal. Chem.*, 86(12): 5661-5666.
7) Voisard et al., 2003, Biotechnol. Bioeng. 82:751-765.
8) Ausubel et al., 1988 and updates, Current Protocols in Molecular Biology, eds. Wiley & Sons, New York.
9) Sambrook et al., 1989 and updates, Molecular Cloning: A Laboratory Manual, Cold Spring Laboratory Press.
10) Remington's Pharmaceutical Sciences, 1995, 18th ed., Mack Publishing Company, Easton, Pa.

The invention claimed is:

1. A method of producing a recombinant protein having decreased galactosylation levels, said method comprising culturing a host cell expressing said protein in cell culture medium comprising a peracetyl galactose, wherein the peracetyl galactose is α-2-fluoro peracetyl galactose (α-2-F peracetyl galactose) or β-2-fluoro peracetyl galactose (β-2-F peracetyl galactose), the host cell is Chinese Hamster Ovary (CHO) cells, and the recombinant protein is an antibody.

2. The method according to claim 1, further comprising purifying said recombinant protein.

3. The method according to claim 1, wherein the peracetyl galactose is β-2-F peracetyl galactose.

4. The method according to claim 1, wherein the peracetyl galactose is α-2-F peracetyl galactose.

5. The method according to claim 1, wherein the concentration of peracetyl galactose in the cell culture medium before seeding is about 0.1 µM to 200 µM.

6. The method according to claim 1, wherein the concentration of peracetyl galactose in the cell culture medium after seeding is about 0.08 µM to 180 µM.

* * * * *

UNITED STATES PATENT AND TRADEMARK OFFICE
CERTIFICATE OF CORRECTION

PATENT NO. : 11,118,208 B2
APPLICATION NO. : 16/300066
DATED : September 14, 2021
INVENTOR(S) : Jordan et al.

It is certified that error appears in the above-identified patent and that said Letters Patent is hereby corrected as shown below:

In the Specification

Column 18,
Line 6, "30 neither" should read --30 µM, neither--.

Column 19,
Line 43, "by 2.0, 4.6" should read --by -2.0, -4.6--.

Column 21,
Line 14, "(–(3-2F-pGal-d5)" should read --(β-2F-pGal-d5)--.
Line 16, "(–(3-2F-pGal-d7)" should read --(β-2F-pGal-d7)--.
Lines 28-29, "(–(3-2F-pGal-d3)" should read --(β-2F-pGal-d3)--.
Line 31, "(–(3-2F-pGal-d5)" should read --(β-2F-pGal-d5)--.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*